United States Patent [19]

Satoh et al.

[11] Patent Number: 4,681,895
[45] Date of Patent: Jul. 21, 1987

[54] NOVEL GUANIDINOMETHYLCYCLOHEXANECARBOXYLIC ACID COMPOUNDS AND ANTI-ULCER DRUG CONTAINING THE SAME

[75] Inventors: Toshio Satoh, Tokushima; Goro Tsukamoto, Toyonaka, both of Japan

[73] Assignee: Kanebo, Ltd., Tokyo, Japan

[21] Appl. No.: 836,711

[22] Filed: Mar. 6, 1986

[30] Foreign Application Priority Data

Jun. 8, 1985 [JP] Japan ............................. 60-47236

[51] Int. Cl.$^4$ .................. A61K 31/245; C07C 129/00
[52] U.S. Cl. .................................... 514/535; 514/563; 514/927; 560/34; 562/439
[58] Field of Search ........................ 560/34; 562/439; 514/535, 563

[56] References Cited

U.S. PATENT DOCUMENTS 4,224,342 9/1980 Fujii et al. ...................... 562/439

FOREIGN PATENT DOCUMENTS 2058773 4/1981 United Kingdom .................. 560/34

OTHER PUBLICATIONS

Nippon Chemiphar Co. Ltd., C. A. 97:66400 g, Jpn. First Publicn. No. 75920/1982.
Nippon Chemphar Co. Ltd., C. A. 98: 178818; Jpn. First Publicn. No. 197256/1982.

Primary Examiner—Howard T. Mars
Assistant Examiner—Bruce D. Gray
Attorney, Agent, or Firm—Wegner & Bretschneider

[57] ABSTRACT

Novel N-phenyl-trans-4-guanidinomethylcyclohexanecarboxamide compounds of the formula:

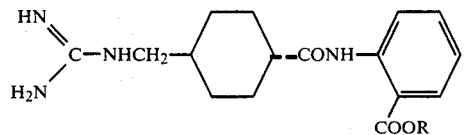

wherein R is hydrogen atom or a lower alkyl group, or a pharmaceutically acceptable salt thereof, which have excellent anti-ulcer activities and hence are useful as an anti-ulcer drug, and a pharmaceutical composition useful for the treatment and prophylaxis of peptic ulcers which comprises as an active ingredient the compound as set forth above in admixture with a conventional pharmaceutically acceptable carrier or diluent.

6 Claims, No Drawings

NOVEL GUANIDINOMETHYLCYCLOHEXANECARBOXYLIC ACID COMPOUNDS AND ANTI-ULCER DRUG CONTAINING THE SAME

The present invention relates to novel guanidinomethylcyclohexanecarboxylic acid compounds and an anti-ulcer drug containing the same. More particularly, it relates to novel N-phenyl-trans-4-guanidinomethylcyclohexanecarboxamide compounds of the formula:

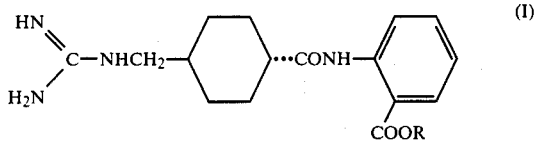

wherein R is hydrogen atom or a lower alkyl, or a pharmaceutically acceptable salt thereof, a process for preparing the same, and an anti-ulcer drug containing the compound as an active ingredient.

PRIOR ART

There have hitherto been known various compounds for the treatment and prophylaxis of peptic ulcers, some of which are the following 4-guanidinomethylcyclohexanecarboxylic acid compounds.

That is, it is disclosed in Japanese Patent First Publication No. 75920/1982 (cf. C.A., 97, 66400q) that trans-4-guanidinomethylcyclohexanecarboxylic acid o-benzyloxycarbonylphenyl ester hydrochloride having the following formula (hereinafter, referred to as "Reference Compound X") shows an anti-ulcer activity.

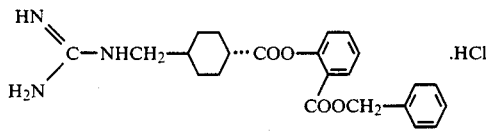

It is also disclosed in Japanese Patent First Publication No. 197256/1982 (cf. C.A., 98, 178818j) that N-phenyl-trans-4-guanidinomethylcyclohexanecarboxamide hydrochloride of the following formula (hereinafter, referred to as "Reference Compound Y") shows an anti-ulcer activity.

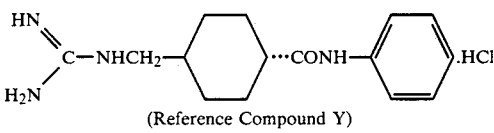

(Reference Compound Y)

BRIEF SUMMARY OF THE INVENTION

In view of the unsatisfactory anti-ulcer activity of these known compounds, the present inventors have intensively studied on finding a novel compound having superior anti-ulcer activity by modifying the chemical structure. As a result, it has now been found that some novel N-phenyl-trans-4-guanidinomethylcyclohexanecarboxamide compounds and pharmaceutically acceptable salts thereof can exhibit potent anti-ulcer activity with less toxicity.

An object of the invention is to provide novel guanidinomethylcyclohexanecarboxylic acid compounds having excellent anti-ulcer activity. Another object of the invention is to provide an excellent anti-ulcer drug containing said novel compound as an active ingredient. These and other objects and advantages of the invention will be apparent to those skilled in the art from the following description.

DETAILED DISCRIPTION OF THE INVENTION

The novel guanidinomethylcyclohexanecarboxamide compounds of the invention have the formula (I) as mentioned hereinbefore, wherein R is hydrogen atom or an alkyl having 1 to 4 carbon atoms, preferably hydrogen atom or an alkyl having 1 to 2 carbon atoms (e.g. methyl or ethyl). The compounds include also a pharmaceutically acceptable salt thereof. The salt includes an acid addition salt, and when R is hydrogen atom, it also includes a salt at the carboxyl group. Suitable examples of the acid addition salt are inorganic acid addition salts such as hydrochloride, sulfate, or phosphate, and organic acid addition salts such as acetate, tartrate, or p-tolulenesulfonate. Suitable examples of the salt at carboxyl group (when R is hydrogen atom) are salts of alkali metals or alkaline earth metals, such as sodium salt, potassium salt, or calcium salt.

The compounds of the invention can be prepared, for instance, by the process as shown in the following Reaction Scheme-1, that is, by reacting trans-4-guanidinomethylcyclohexanecarboxylic acid of the formula (II), or an acid addition salt thereof, or a reactive derivative thereof with anthranilic acid or an ester thereof of the formula (III), and when R is hydrogen atom, optionally followed by subjecting the resulting compound to hydrolysis to give a free acid compound of the formula (I') or a salt thereof.

[Reaction Scheme-1]

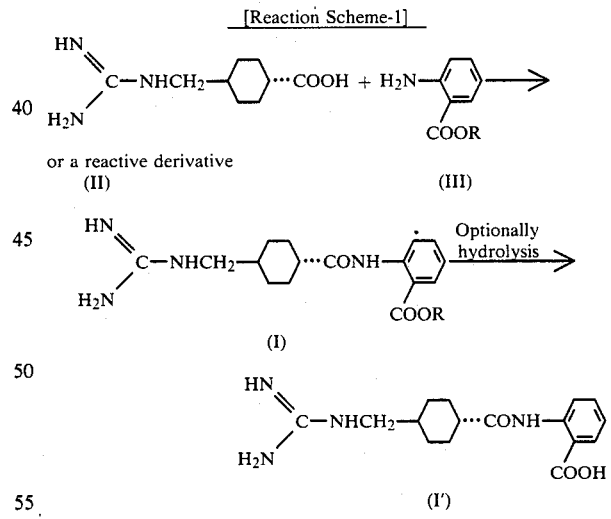

wherein R is as defined above.

In the above Reaction scheme-1, the reaction of trans-4-guanidinomethylcyclohexanecarboxylic acid (II) or a salt thereof and anthranilic acid or an ester thereof (III) is usually carried out in the presence of a condensation agent such as dicyclohexylcarbodiimide in an anhydrous organic solvent (e.g. acetone, tetrahydrofuran, dioxane, pyridine, dimethylformamide, etc.) The compound (III) and condensation agent are used each in an amount of 1.0 to 1.5 mole to 1.0 mole of the compound (II). The reaction is carried out at arround room temperature for 10 to 80 hours.

In the above reaction, when the reaction of an acid addition salt of the compound (II) with the compound (III) is carried out in the absence of a basic substance or in the presence of very weak base such as pyridine, the compound (I) is obtained in the form of an acid addition salt thereof.

The trans-4-guanidinomethylcyclohexanecarboxylic acid (II) can be used in the form of a reactive derivative, for example, a mixed acid anhydride, which can be prepared by the reaction of the compound (II) or a salt thereof with a chloroformic acid ester (e.g. ethyl chloroformate, isobutyl chloroformate, etc.), a carboxylic acid chloride (e.g. isovaleroyl chloride, pivaloyl chloride, etc.), or a sulfonic acid chloride (e.g. p-toluenesulfonyl chloride, etc.). The mixed acid anhydride can usually be prepared by reacting 1 mole of trans-4-guanidinomethylcyclohexanecarboxylic acid or an acid addition salt thereof with 1.0 to 1.5 mole of the above chloroformic acid ester, carboxylic acid chloride or sulfonic acid chloride in the presence of a tertiary amine (e.g. triethylamine, N-methylmorpholine, etc.) in an anhydrous organic solvent (e.g. dimethylformamide, tetrahydrofuran, dioxane, pyridine, dimethylsulfoxide, etc.). The reaction is carried out at a temperature of $-30°$ to $20°$ C., preferably $-20°$ to $10°$ C., for 5 minutes to one hour. The tertiary amine is usually used in an amount of 1.0 to 1.1 mole to 1 mole of the chloroformic acid ester, carboxylic acid chloride or sulfonic acid chloride.

The mixed acid anhydride prepared above can be used for the reaction with the compound (III) without isolation from the reaction mixture. That is, the compound (III) is added to the reaction mixture obtained above wherein the mixed acid anhydride is contained, and the mixture is stirred at a temperature from $-20°$ C. to room temperature for 2 to 24 hours, by which the compound (I) or a salt thereof is produced. In the above reaction, the compound (III) is used in an amount of 1.0 to 2.5 mole, preferably 1.0 to 1.5 mole, to 1.0 mole of the trans-4-guanidinomethylcyclohexanecarboxylic acid (II) or a salt thereof used for the preparation of the mixed acid anhydride. The compound (III) is usually used in the form of a solution or suspension in an appropriate solvent, such as an aprotic solvent (e.g. dimethylformamide, pyridine, tetrahydrofuran, dimethylsulfoxide, etc.) or a protic solvent (e.g. a lower alcohol such as methanol or ethanol, water, or a mixture thereof).

As is shown in the above Reaction Scheme-1, when the R is a lower alkyl in the compound (I) or a salt thereof thus obtained, the compound (I) or a salt thereof can optionally be subjected to hydrolysis to give the compound (I') or a salt thereof, i.e. the compound of the formula (I) wherein R is hydrogen atom, or a salt thereof. The hydrolysis is carried out by treating the compound (I) wherein R is a lower alkyl or a salt thereof with 1 to 4 equivalent of an alkali in a water-soluble organic solvent. The alkali includes, for example, alkali metal hydroxides (e.g. sodium hydroxide, potassium hydroxide, etc.), and the water-soluble organic solvent includes, for example, a lower alcohol (e.g. methanol, ethanol, etc.). The hydrolysis is usually carried out at a temperature from 40° to 80° C., preferably 50° to 60° C., for 30 minutes to 5 hours.

The compound (I') or a salt thereof can also be prepared by a process as shown in the following Reaction Scheme-2, that is, by reacting a compound of the formula (II) or a salt thereof or a reactive derivative thereof with benzyl anthranilate (III'), followed by hydrogenolysis of the resulting compound (I″) in order to remove the benzyl group.

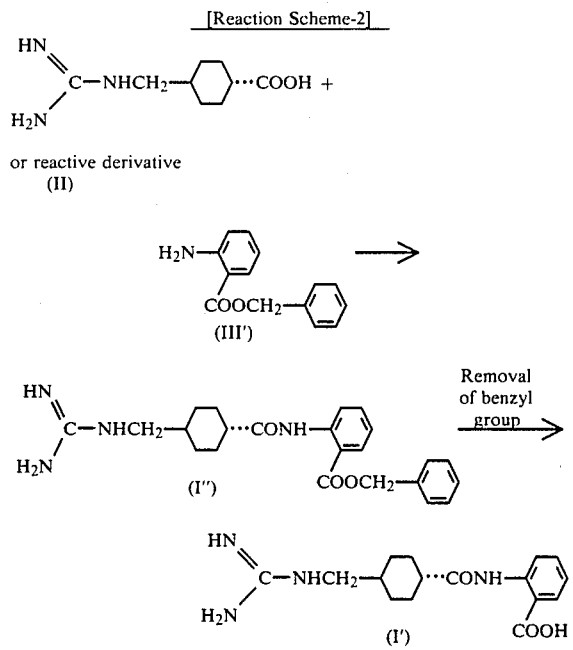

In the above Reaction Scheme-2, the reaction of the compound (II), or a salt thereof or a reactive derivative thereof with the compound (III') is carried out in the same manner as described in the reaction of the compound (II) with the compound (III) in Reaction Scheme-1. The removal of benzyl group from the resulting compound (I″) or a salt thereof can be carried out by hydrogenolysis thereof in a usual manner for the removal of benzyl group.

That is, the hydrogenolysis of the compound (I″) or a salt thereof is usually carried out by contacting the compound with hydrogen gas of a pressure from atmospheric pressure to 20 kg/cm$^2$ in the presence of a catalyst in a solvent. The catalyst includes any conventional catalyst used for hydrogenolysis, for example, palladium-carbon, palladium black, platinum black, and the like, which is usually used in an amount of 1 to 30 % (w/w) based on the weight of the compound (I″) or a salt thereof. Suitable examples of the solvent are alcohols (e.g. methanol, ethanol, etc.), and a mixture with the alcohol with water. The hydrogenolysis reaction is carried out by stirring or shaking the reaction mixture at a temperature from room temperature to 40° C. for 30 minutes to 3 hours under hydrogen gas. When the hydrogenolysis is carried out by treating an acid addition salt of the compound (I″) under non-basic condition, the desired compound (I') is obtained in the form of an acid addition salt.

The compounds (I) or a salt thereof prepared by the above processes can be purified by conventional purification methods such as recrystallization. They may optionally be converted into a pharmaceutically acceptable salt thereof by a conventional method.

The compounds (I) or a pharmaceutically acceptable salt thereof have excellent anti-ulcer activity and hence are used as an anti-ulcer agent, which is usually used by oral administration. The compounds of the present invention are usually used in conventional pharmaceutical preparations, such as powders, granules, tablets, capsules, and the like. These preparations are prepared by admixing the active compounds (I) or a pharmaceutically acceptable salt thereof with conventional pharmaceutically acceptable carriers or diluents, such as starches, lactose, crystalline cellulose, kaoline, calcium carbonate, talc, and the like.

The dose of the active compounds (I) or a pharmaceutically acceptable salt thereof may vary depending on the age, weight or sex of the patients, severity of disease and kinds of the preparations, but is usually in the range of 30 to 1,500 mg per day in adult.

The pharmacological activities of the compounds (I) or a salt thereof of the present invention are illustrated by the following experiments.

Experiment 1

Activity against stress-induced gastric ulcer

Compounds to be tested are as follows:

1. Compound A (a compound of this invention):
N-(o-Ethoxycarbonylphenyl)-trans-4-guanidinomethylcyclohexanecarboxamide hydrochloride monohydrate (the compound of Example 1)

2. Compound B (a compound of this invention):
N-(o-Methoxycarbonylphenyl)-trans-4-guanidinomethylcyclohexanecarboxamide hydrochloride monohydrate (the compound of Example 2)

3. Compound C (a compound of this invention):
N-(o-Carboxyphenyl)-trans-4-guanidinomethylcyclohexanecarboxamide hydrochloride monohydrate (the compound of Example 3)

4. Reference Compound X:
Trans-4-guanidinomethylcyclohexanecarboxylic acid o-benzyloxycarbonylphenyl ester hydrochloride (disclosed in Japanese Patent First Publication No. 75920/1982)

5. Reference Compound Y:
N-Phenyl-trans-4-guanidinomethylcyclohexanecarboxamide hydrochloride (disclosed in Japanese Patent First Publication No. 197256/1982)

Method

The experiment was carried out by a modified method of that of Takagi and Okabe [cf. Jap. J. Pharmacol., 18, 9 (1968)].

Male Sprague-Dawley rats weighing 180–200 g (8 week old), 6–8 per group, were fasted for 24 hours and administered orally with each test compound which was suspended in 1% arabic gum aqueous solution. After 15 minutes, the animals were placed in a stress cage and immerse vertically to the level of the xiphoid process in a water bath kept at 23° C. for 17 hours. The animals were killed by ether inhalation. The stomach of each rat was removed, inflated by injecting 12 ml of 1% formalin, and immersed in 1% formalin for 15 minutes. The stomach was then incised along the greater curvature and examined for lesions in the glandular portion under a dissecting microscope. The length (mm) of a ulcer was totalled on each animal and it was indicated as the ulcer index. The mean ulcer index (m) in each test compound-treated group was calculated.

The control animals received the same procedure without administering of test compound and the mean ulcer index (l) was calculated.

Inhibitory ratio of test compound is expressed as follows.

Inhibitory ratio $(\%) = (1 - m/l) \times 100$ wherein l is mean ulcer index in control group, and m is mean ulcer index in test compound-treated group.

The anti-ulcer activity of test compound ($ED_{50}$) was calculated by dose-response curve.

Results

The results are shown in Table 1.

Experiment 2

Activity against ethanol-induced gastric ulcer

The same test compounds as used in Experiment 1 were used.

Method

The experiment was carried out according to the method of Robert et al. [cf. Gastroenterology, 77, 433 (1979)].

Male Sprague-Dawley rats weighing 180–200 g (8 week old), 6–8 per group, were fasted for 24 hours and administered orally with each test compound which was suspended in 1% arabic gum aqueous solution. After 30 minutes, 99.5% ethanol (as a necrotizing agent) was given orally to the rats in a volume of 1 ml. The animals were killed by ether inhalation 1 hour after receiving of ethanol. The stomach of each rat was removed, inflated by injecting 12 ml of 1 % formalin, and immersed in 1% formalin for 15 minutes. Afterward, the mean ulcer index and inhibitory ratio were calculated by the same method as in Experiment 1, and then the $ED_{50}$ was calculated by dose-response curve.

Results

The results are shown in Table 1.

Experiment 3

Activity against indomethacin-induced gastric ulcer

The same test compounds as used in Experiment 1 were used.

Method

The experiment was carried out by a modified method of that of Okabe et al. [cf. Dig. Dis. Sci., 28, 1034 (1983)].

Male Sprague-Dawley rats weighing 180–200 g (8 week old), 6–8 per group, were fasted for 24 hours and administered orally with each test compound which was suspended in 1% arabic gum aqueous solution. After 15 minutes, indomethacin (in a solution in 3% sodium bicarbonate solution) was given subcutaneously to the rats at a dose of 30 mg/kg. The animals were killed by ether inhalation 5 hours after receiving of indomethacin. The stomach of each rat was removed, inflated by injecting 12 ml of 1% formalin, containing 0.1% pontamine sky blue, and immersed in 1% formalin for 15 minutes. Afterward, the mean ulcer index and inhibitory ratio were calculated by the same method as in Experiment 1, and then $ED_{50}$ was calculated by dose response curve.

Results

The results are shown in Table 1.

Experiment 4

Test of acute toxity [minimum lethal dose (MLD)]

The same test compounds as used in Experiment 1 were used.

Method

Male ddY mice weighing 20–22 g (4 week old), 5 per group, were fasted for 17 hours and administered orally with each test compound which was suspended in 1% arabic gum aqueous solution. The animals were observed for 7 days, and the minimum lethal dose (MLD) was calculated.

Results

The results are shown in Table 1.

TABLE 1

| Test compd. | $ED_{50}$ (mg/kg) Anti-stress-induced ulcer | Anti-ethanol-induced ulcer | Anti-indo-methacin-induced ulcer | MLD (mg/kg) (acute toxicity) |
| --- | --- | --- | --- | --- |
| Compd. A | 108 | 36 | 33 | >3,000 |
| Compd. B | 118 | 42 | 40 | >3,000 |
| Compd. C | 114 | 41 | 37 | >3,000 |
| Compd. X | 376 | 108 | 103 | >3,000 |
| Compd. Y | 135 | 199 | 86 | <1,000 |

As is clear from the above experimental results, the compounds of the present invention show greater potent anti-ulcer activities against various ulcers, such as stress-induced, ethanol-induced and indomethacin-induced gastric ulcers in comparison with the reference compounds, and show lower toxicity.

The preparation of the compounds of the present invention is issustrated by the following Examples.

EXAMPLE 1

Preparation of N-(o-ethoxycarbonylphenyl)-trans-4-guanidinomethylcyclohexanecarboxamide hydrochloride:

Trans-4-guanidinomethylcyclohexanecarboxylic acid hydrochloride (10.0 g, 0.042 mole) (which is prepared by the method as disclosed in Japanese Patent First Publication No. 19694/1977, C.A., 87, 53269x) and ethyl anthranilate (10.4 g, 0.063 mole) are added to pyridine (50 ml), and the mixture is stirred for a while, and thereto is added dicyclohexylcarbodiimide (13 g, 0.063 mole), and the mixture is stirred at room temperature for 72 hours. After the completion of the reaction, water (30 ml) is added to the reaction mixture, and the mixture is stirred for 30 minutes, and the undissolved materials are filtered off. The filtrate is concentrated to dryness. The resulting residue is washed with ethyl acetate (300 ml) and recrystallized from water to give the title compound (6.74 g) as white crystals. m.p. 92°–95° C.

IR(KBr)$\nu$max(cm$^{-1}$): 3500–3000, 1670, 1610

NMR (DMSO-d$_6$)$\delta$: 0.9–2.4 (10H, m, proton in cyclohexane ring), 1.3 (3H, t, CH$_2$CH$_3$), 2.9–3.1 (2H, br, NHCH$_2$), 4.3 (2H, q, CH$_2$CH$_3$), 7.0–8.4 (9H, m, proton in benzene ring and guanidinium proton), 10.7 (1H, s, CONH)

Elementary analysis for C$_{18}$H$_{26}$N$_4$O$_3$.HCl.H$_2$O; Calcd. (%): C,53.93; H,7.29; N,13.98; Found (%): C,53.61; H,7.41; N,13.84.

EXAMPLE 2

Preparation of N-(o-methoxycarbonylphenyl)-trans4-guanidinomethylcyclohexanecarboxamide hydrochloride:

Trans-4-guanidinomethylcyclohexanecarboxylic acid hydrochloride (3 g, 0.013 mole) (which is prepared by the method as disclosed in Japanese Patent First Publication No. 19694/1977, C.A., 87, 53269x) and methyl anthranilate (2.3 g, 0.015 mole) are added to pyridine (20 ml), and the mixture is stirred for a while, and thereto is added dicyclohexylcarbodiimide (3.1 g, 0.015 mole), and the mixture is stirred at room temperature for 72 hours. After the completion of the reaction, water (10 ml) is added to the reaction mixture, and the mixture is stirred for 30 minutes, and the undissolved materials are filtered off. The filtrate is concentrated to dryness. The resulting residue is washed with ethyl acetate (100 ml) and recrystallized from water to give the title compound (2.23 g) as white crystals. m.p. 118.5°–120.5° C.

IR(KBr)$\nu$max(cm$^{-1}$): 3600–3000, 1670, 1625, 1605

NMR (DMSO-d$_6$)$\delta$: 0.8–2.4 (10H, m, proton in cyclohexane ring), 2.9–3.1 (2H, br, NHCH$_2$), 3.95 (3H, s, COOCH$_3$) 7.1–8.4 (9H, m, proton in benzene ring and guanidinium proton), 10.7 (1H, s, CONH)

Elementary analysis for C$_{17}$H$_{24}$N$_4$O$_3$.HCl.H$_2$O; Calcd. (%): C,52.78; H,7.03; N,14.48; Found (%): C,53.04: H,7.29: N,14.54.

EXAMPLE 3

Preparation of N-(o-carboxyphenyl)-trans-4-guanidinomethylcyclohexanecarboxamide hydrochloride:

The title compound is prepared by the following step 1 to step 2.

(i) Step 1

Trans-4-guanidinomethylcyclohexanecarboxylic acid hydrochloride (3.0 g, 0.013 mole) (which is prepared by the method as disclosed in Japanese Patent First Publication No. 19694/1977, C.A., 87, 53269x) and benzyl anthranilate (3.4 g, 0.015 mole) are added to pyridine (25 ml), and thereto is added dicyclohexylcarbodiimide (3.1 g, 0.015 mole), and the mixture is stirred at room temperature for 72 hours. After the completion of the reaction, water (10 ml) is added to the reaction mixture, and the mixture is stirred for 30 minutes, and the undissolved materials are filtered off. The filtrate is concentrated to driness. The resulting residue is washed with ethyl acetate (100 ml) and recrystallized from water to give N-(o-benzyloxycarbonylphenyl)-trans-4-guanidinomethylcyclohexanecarboxamide hydrochloride (3.2 g) as white crystals. m.p. 93°–95° C.

IR(KBr)$\nu$max(cm$^{-1}$): 3400–2800, 1710–1600

NMR (DMSO-d$_6$)$\delta$: 0.8–2.4 (10H, m, proton in cyclohexane ring), 2.9–3.1 (2H, br, NHCH$_2$), 5.35 (2H, s,

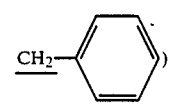

7.1–8.4 (14H, m, proton in benzene ring and guanidinium proton), 10.6 (1H, s, CONH)

Elementary analysis for C$_{23}$H$_{28}$N$_4$O$_3$ HCl.H$_2$O Calcd. (%): C,59.67; H,6.75; N,12.10 Found (%): C,59.81; H,6.86; N,12.13

(ii) Step 2

The above N-(o-benzyloxycarbonylphenyl)-trans-4-guanidinomethylcyclohexylcarboxamide hydrochloride (1.09 g, 0.0024 mole) is dissolved in methanol (50 ml), and thereto is added 10% palladium-carbon (0.23 g), and the mixture is stirred with blowing hydrogen gas under atmospheric pressure at 30° C. for one hour. After the completion of the reaction, palladium-carbon is filtered off, and the filtrate is concentrated under reduced pressure. The resulting residue is recrystallized from a mixture of methanol-water to give N-(o-carboxyphenyl)-trans-4-guanidinomethylcyclohexanecarboxamide hydrochloride (0.76 g) as white crystals, melting at around 135°–145° C. and after being solidified, decomposing at 215°–220° C.

IR(KBr)$\nu$max(cm$^{-1}$): 3500–2800, 1680, 1650, 1610

NMR (DMSO-d$_6$)$\delta$: 0.8–2.4 (10H, m, proton in cyclohex ring), 2.8–3.2 (2H, br, NHCH$_2$), 6.9–8.6 (10H, m, COOH, proton in benzene ring and guanidinium proton), 11.3 (1H, s, CONH)

Elementary analysis for C$_{16}$H$_{22}$N$_4$O$_3$.HCl.H$_2$O; Calcd. (%): C,51.54; H,6.76; N,15.03; Found (%): C,51.30; H,6.93; N,14.86.

EXAMPLE 4

Preparation of N-(o-carboxyphenyl)-trans-4-guanidinomethylcyclohexanecarboxamide:

To N-(o-ethoxycarbonylphenyl)-trans-4-guanidinomethylcyclohexanecarboxamide hydrochloride (25.4 g, 0.063 mole) (which is prepared in the same manner as described in Example 1) is added methanol (130 ml), and the mixture is heated to 50° C., and thereto is added a solution of NaOH (7.16 g, 0.179 mole) in water (65 ml), and the mixture is stirred at 50°–60° C. for 45 minutes. The reaction mixture is ice-cooled, and the white precipitates are separated by filtration, suspended in methanol (100 ml) and dissolved by adding thereto 4N-hydrochloric acid (21 ml). After evaporation of the solvent under reduced pressure, the residue is recrystallized from water-methanol (4:1), and the crystals thus obtained are again recrystallized from water-methanol (3:1) to give N-(o-carboxyphenyl)-trans-4-guanidinomethylcyclohexanecarboxamide hydrochloride (19.3 g) as white crystals. The physical data of this compound are identical with those of N-(o-carboxyphenyl)-trans-4-guanidinomethylcyclohexanecarboxamide hydrochloride as obtained in Example 3.

The N-(o-carboxyphenyl)-trans-4-guanidinomethylcyclohexanecarboxamide hydrochloride (5.0 g, 0.013 mole) obtained above is dissolved in methanol (30 ml) and the mixture is added under ice-cooling to a solution of NaOH (3.25 g, 0.0813 mole) in water (10 ml), and the mixture is stirred under ice-cooling for 30 minutes and further stirred at room temperature for 2 hours. The resulting precipitates are taken by filtration and dissolved in acetic acid (50 ml). After evaporation of the solvent under reduced pressure, the residue is washed with methanol and recrystallized from acetic acid-water to give N-(o-carboxyphenyl)trans-4-guanidinomethylcyclohexanecarboxamide (2.5 g). m.p. 300°–310° C. (decomp.)

IR(KBr)$\nu$max(cm$^{-1}$): 3400–2900, 1670, 1640, 1590

NMR (DMSO-d$_6$)$\delta$: 0.8–2.4 (10H, m, proton in cyclohexane ring), 2.8–3.2 (2H, br, NHCH$_2$), 6.9–8.6 (9H, m, proton in benzene ring and guanidinium proton), 9.95 (1H, s, CONH)

Elementary analysis for C$_{16}$H$_{22}$N$_4$O$_3$.0.5H$_2$O; Calcd. (%): C,58.70; H,7.08; N,17.11; Found (%): C,58.70; H,7.09; N,17.07.

EXAMPLE 5

Preparation o N-(o-carboxyphenyl)-trans-4-guanidinomethylcyclohexanecarboxamide hydrochloride:

Trans-4-guanid nomethylcyclohexanecarboxylic acid hydrochloride (1.11 g, 0.005 mole) (which is prepared by the method as disclosed in Japanese Patent First Publication No. 19694/1977, C.A., 87, 53269x) is dissolved in dimethylformamide (30 ml), and the mixture is cooled to $-15°$ C. To the mixture are added dropwise ethyl chloroformate (0.54 g, 0.005 mole) and then triethylamine (0.51 g, 0.005 mole). After stirring the mixture at $-15°$ to $-10°$ C. for 5 minutes, a solution of anthranilic acid (0.69 g, 0.005 mole) and triethylamine (0.51 g, 0.005 mole) in dimethylformamide (10 ml) is added to the mixture, and the mixture is stirred at $-10°$ to 0° C. for 3 hours and further stirred at room temperature for 15 hours. Thereafter, dimethylformamide is evaporated under reduced pressure, and to the residue is added water (10 ml) and further concentrated hydrochloric acid to regulate to about pH 1. The reaction mixture is allowed to stand at room temperature, and the resulting precipitates are recrystallized from water-methanol to give N-(o-carboxyphenyl)-trans-4-guanidinomethylcyclohexanecarboxamide hydrochloride (0.61 g) as white crystals. The physical data of this compound are identical with those of N-(o-carboxyphenyl)-trans-4-guanidinomethylcyclohexanecarboxamide hydrochloride prepared in Example 3.

EXAMPLE 6

Preparation of N-(o-methoxycarbonylphenyl)-trans-4-guanidinomethylcyclohexanecarboxamide hydrochloride:

Trans-4-guanidinomethylcyclohexanecarboxylic acid hydrochloride (111 g, 0.5 mole) (which is prepared by the method as disclosed in Japanese Patent First Publication No. 19694/1977, C.A., 87, 53269x) and methyl anthranilate (75.6 g, 0.5 mole) are dissolved in a mixture of dimethylformamide and pyridine (1:1, 1250 ml), and thereto is added dicyclohexylcarbodiimide (103 g, 0.5 mole), and the mixture is stirred at room temperature for 40 hours. After the undissolved materials are filtered off, the solvent is evaporated under reduced pressure. To the residue are added methanol (500 ml) and water (80 ml), and the mixture is stirred, and the undissolved materials are again filtered off and the solvent is evaporated under reduced pressure. The resulting residue is washed with acetone (2000 ml) and recrystallized from water to give the title compound (143 g) as white crystals. The physical data of this compound are identical with those of N-(o-methoxycarbonylphenyl)-trans-4-guanidinomethylcyclohexanecarboxamide hydrochloride prepared in Example 2.

EXAMPLE 7

Preparation of N-(o-ethoxycarbonylphenyl)-trans-4-guanidinomethylcyclohexanecarboxamide acetate:

N-(o-Ethoxycarbonylphenyl)-trans-4-guanidinomethylcyclohexanecarboxamide hydrochloride (370 mg, 0.001 mole) prepared in Example 1 is dissolved in a mixture of water-methanol (1:1) and thereto is added ion exchange resin (Amberlite ®IRA-400, manufactured by Rohm & Haas, which is previously converted into acetate type) (15 ml), and the mixture is stirred at room temperature overnight. After filtering off the resin, the filtrate is concentrated and recrystallized from water to give the title compound (300 mg) as white crystals. m.p. 212°–214° C.

IR(KBr)$\nu$max(cm$^{-1}$): 3400–2900, 1700, 1680, 1610

NMR (DMSO-d$_6$)$\delta$: 0.8–2.3 (10H, m, proton in cyclohexane ring), 1.3 (3H, t, CH$_2$CH$_3$), 1.7 (3H, s, CH$_3$COO), 2.8–3.0 (2H, br, NHCH$_2$), 4.3 (2H, q, CH$_2$CH$_3$), 6.9–8.5 (9H, m, proton in benzene ring and guanidinium proton), 10.4–11.1 (1H, br, CONH)

Elementary analysis for C$_{18}$H$_{26}$N$_4$O$_3$.CH$_3$COOH.H$_2$O; Calcd. (%): C,56.59; H,7.60; N,13.20; Found (%): C,56.38; H,7.82; N,13.36.

EXAMPLE 8

Preparation of tablets:

| [Formulation] | |
|---|---|
| Compound A of this invention (compound in Ex. 1) | 50 g |
| Lactose | 10 g |
| Corn starch | 30 g |
| Crystalline cellulose | 8 g |
| Hydroxypropyl cellulose | 1 g |
| Magnesium stearate | 1 g |
| | 100 g |

[Method]

Compound A of this invention, lactose, corn starch and crystalline cellulose are mixed, and thereto is added a solution of hydroxypropyl cellulose in water (30 ml), and the mixture is well kneaded. The kneaded mixture is granulated by passing through a screen (20 mesh) to give granules. After drying, the granules are mixed with magnesium stearate, and the mixture is tableted (each tablet: 100 mg).

EXAMPLE 9

Preparation of capsules:

| [Formulation] | |
|---|---|
| Compound B of this invention (compound in Ex. 2) | 100 g |
| Lactose | 100 g |
| Corn starch | 50 g |
| Crystalline cellulose | 47 g |
| Magnesium stearate | 3 g |
| | 300 g |

[Method]

The above ingredients are mixed well, and the mixture is packed into #2 capsules (each content: 300 mg) to give the desired capsule preparations.

EXAMPLE 10

Preparation of granules:

| [Formulation] | |
|---|---|
| Compound C of this invention (compound in Ex. 3) | 100 g |
| Lactose | 470 g |
| Corn starch | 400 g |
| Hydroxypropyl cellulose | 30 g |
| | 1000 g |

[Method]

Compound C, lactose and corn starch are mixed and thereto is added a solution of hydroxypropyl cellulose in water (400 ml), and the mixture is kneaded well. The kneaded mixture is granulated by passing through a screen (20 mesh) to give granules. After drying, the granules are made uniform size to obtain the desired granule preparation.

What is claimed is:

1. An N-phenyl-trans-4-guanidinomethylcyclohexanecarboxamide compound of the formula:

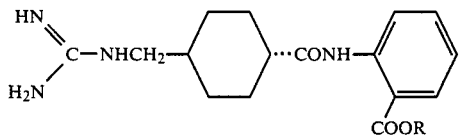

wherein R is hydrogen atom or a lower alkyl group, and a pharmaceutically acceptable salt thereof.

2. The compound according to claim 1, wherein R is hydrogen atom, or a pharmaceutically acceptable salt thereof.

3. The compound according to claim 1, wherein R is methyl group, or a pharmaceutically acceptable salt thereof.

4. The compound according to claim 1, wherein R is ethyl group, or a pharmaceutically acceptable salt thereof.

5. A pharmaceutical composition for the treatment or prophylaxis of peptic ulcer, which comprises as an active ingredient an effective amount of an N-phenyl-trans-4-guanidinomethylcyclohexanecarboxamide of the formula:

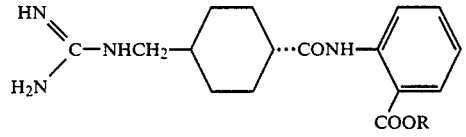

wherein R is hydrogen atom or a lower alkyl group, or a pharmaceutically acceptable salt thereof in admixture with a conventional pharmaceutically acceptable carrier or diluent.

6. The composition according to claim 5, wherein the active ingredient is a compound of the formula (I) wherein R is hydrogen atom, or a pharmaceutically acceptable salt thereof.

* * * * *

UNITED STATES PATENT AND TRADEMARK OFFICE
CERTIFICATE OF CORRECTION

PATENT NO. : 4,681,895

DATED : July 21, 1987

INVENTOR(S) : Toshio Satoh and Goro Tsukamoto

It is certified that error appears in the above-identified patent and that said Letters Patent is hereby corrected as shown below:

Column 10, line 10, replace "Preparation o" with --Preparation of--.

Column 10, line 13, replace "Trans-4-guanid nomethylcyclohexanecarboxylic" with --Trans-4-guanidinomethylcyclohexanecarboxylic--.

Signed and Sealed this

Twelfth Day of January, 1988

Attest:

DONALD J. QUIGG

Attesting Officer

Commissioner of Patents and Trademarks